(12) United States Patent
Xu et al.

(10) Patent No.: US 10,028,914 B2
(45) Date of Patent: Jul. 24, 2018

(54) REDUCTION TYPE COENZYME Q10 POWDER, COMPOSITION THEREOF, AND PREPARATION METHOD THEREOF

(71) Applicant: Zhejiang Medicine Co., Ltd. Xinchang Pharmaceutical Factory, Xinchang County (CN)

(72) Inventors: Xinde Xu, Xinchang County (CN); Gang Chen, Xinchang County (CN); Xuejun Lao, Xinchang County (CN); Lihua Zhang, Xinchang County (CN); Xiaoxia Sun, Xinchang County (CN); Xiaoyue Jiang, Xinchang County (CN)

(73) Assignee: ZHEJIANG MEDICINE CO., LTD. XINCHANG PHARMACEUTICA FACTORY, Zhejiang (CN)

( * ) Notice: Subject to any disclaimer, the term of this patent is extended or adjusted under 35 U.S.C. 154(b) by 0 days.

(21) Appl. No.: 14/786,974

(22) PCT Filed: Mar. 14, 2014

(86) PCT No.: PCT/CN2014/000269
§ 371 (c)(1),
(2) Date: Oct. 25, 2015

(87) PCT Pub. No.: WO2014/173174
PCT Pub. Date: Oct. 30, 2014

(65) Prior Publication Data
US 2016/0101053 A1    Apr. 14, 2016

(30) Foreign Application Priority Data

Apr. 25, 2013 (CN) .......................... 2013 1 0161260

(51) Int. Cl.
| | | |
|---|---|---|
| *A61K 31/122* | (2006.01) | |
| *A61K 9/16* | (2006.01) | |
| *C07C 41/26* | (2006.01) | |
| *C07C 41/34* | (2006.01) | |
| *A61K 9/00* | (2006.01) | |
| *A61K 9/48* | (2006.01) | |
| *A61K 31/09* | (2006.01) | |
| *C12P 7/66* | (2006.01) | |
| *A23L 33/10* | (2016.01) | |

(52) U.S. Cl.
CPC ............ *A61K 9/1617* (2013.01); *A23L 33/10* (2016.08); *A61K 9/0053* (2013.01); *A61K 9/1652* (2013.01); *A61K 9/1658* (2013.01); *A61K 9/4858* (2013.01); *A61K 9/4866* (2013.01); *A61K 9/4875* (2013.01); *A61K 31/09* (2013.01); *C07C 41/26* (2013.01); *C07C 41/34* (2013.01); *C12P 7/66* (2013.01); *A23V 2002/00* (2013.01)

(58) Field of Classification Search
None
See application file for complete search history.

(56) References Cited

U.S. PATENT DOCUMENTS

2007/0243180 A1* 10/2007 Tanaka ................. A61K 9/1652
424/94.1
2008/0026063 A1* 1/2008 Ueda .................... A61K 9/4875
424/488

FOREIGN PATENT DOCUMENTS

CN    101272769 A  *  9/2008   ........... A61K 9/1617

OTHER PUBLICATIONS

English Translation of CN101272769A retrieved from Espacenet on Dec. 20, 2016.*

* cited by examiner

Primary Examiner — Jessica Worsham
(74) Attorney, Agent, or Firm — Ash Tankha; Lipton, Weinberger & Husick

(57) ABSTRACT

The present invention describes a reduction type coenzyme Q10 powder, a composition thereof, and a preparation method thereof. The reduction type coenzyme Q10 powder is obtained by reacting an oxidation type coenzyme Q10 with the presence of a reducing agent, removing an organic solvent and other purities from a reaction solution after the reaction is finished to obtain an oil-soluble reduction type coenzyme Q10 liquid, and then directly performing prill formation with cold wind on an obtained reduction type coenzyme Q10 greasy substance. The obtained reduction type coenzyme Q10 powder has a lower crystallinity, and in a Cu-K[alpha] X-ray diffraction spectrum, has a strong peak at a diffraction angle 2[theta] being 18.9 DEG, and has a very strong absorption peak at a diffraction angle 2[theta] being 22.8 DEG. The reduction type coenzyme Q10 powder obtained in the present invention is in an incompletely crystallized state, has desirable stability and desirable oral bioavailability, and is suitable for use in applications such as dietary supplements, cosmetics or pharmaceuticals.

5 Claims, 3 Drawing Sheets

REDUCTION TYPE COENZYME Q10 POWDER, COMPOSITION THEREOF, AND PREPARATION METHOD THEREOF

CROSS-REFERENCE TO RELATED APPLICATIONS

This application is a national phase application of the PCT international application number PCT/CN2014/000269 titled "REDUCTION TYPE COENZYME Q10 POWDER, COMPOSITION THEREOF, AND PREPARATION METHOD THEREOF", filed in the State Intellectual Property Office of the People's Republic of China on Mar. 14, 2014, which claims priority to and the benefit of Chinese patent application number 201310161260.2, filed in the State Intellectual Property Office of the People's Republic of China on Apr. 25, 2013. The specifications of the above referenced patent applications are incorporated herein by reference in their entirety.

FIELD OF THE INVENTION

The present invention relates to a reduction type coenzyme Q10 powder with high bioavailability. More specifically, the present invention relates to preparation method of the reduction type coenzyme Q10 powder and composition thereof in an incomplete crystallization condition with high bioavailability.

BACKGROUND OF THE INVENTION

Coenzyme Q10 is a fat-soluble compound widely existed in organisms and is widely distributed in nature, mainly in yeast, plant leaves, seeds and cells of heart, liver and kidney of animals. Coenzyme Q10 is one of the most important coenzyme in human body. The main function of coenzyme Q10 is to scavenge free radicals, anti-tumor, enhance immunity, promote metabolism and improve hypoxia tolerance of heart, etc.

The existing states of coenzyme Q10 are usually in two kinds of oxidized coenzyme Q10 and reduced coenzyme Q10. Reduced coenzyme Q10 is referred to as Ubiquinol with a white crystal. Oxidized coenzyme Q10 is referred to as Ubiquinone with a yellow crystal. Their structural formulas are as follows:

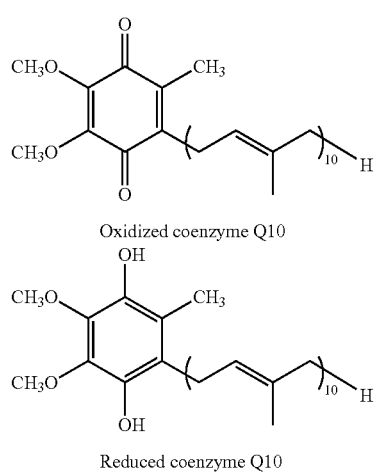

Oxidized coenzyme Q10

Reduced coenzyme Q10

Reduced coenzyme Q10 is an important cell metabolism activator to breathe and immunopotentiator, and has effects of inoxidizability, scavenging free radicals, beauty skin care, reducing blood sugar, decompression, preventing vascular atherosclerosis, improving chronic respiratory disease and so on. In comparison with oxidized coenzyme Q10, reduced coenzyme Q10 has higher absorptivity and higher bioavailability. Reduced coenzyme Q10 has been widely used in the field of pharmaceuticals, health foods, foods, cosmetics and so on.

Sources of reduced coenzyme Q10 in the art can basically be divided into three categories such as chemical synthesis, microbial fermentation, animals extracts and plants extracts. In industry, oxidized coenzyme Q10 is always obtained by reduction reaction in the presence of reductant and crystallization in an organic solvent such as alcohol after the reduction reaction. US2004019788A1 describes a method for crystallization of reduced coenzyme Q10 in aqueous solution such as organic solvent replaced by water or mixture of water and organic solvent. US 20050074860 A1 also describes a method of dissolving reduced coenzyme Q10 crystal in oil and recrystallization after cooling to obtain a new crystal. It was reported that crystal was changed and its bioavailability was improved. It can be seen from the X-ray diffraction pattern that two of crystals are in small proportion and in less bioavailability. Moreover, it is difficult to remove vegetable oil on the surface of crystals obtained by this method; or it needs a lot of toxic solvents such as n-hexane washing to remove the vegetable oil on the surface of crystals. These limit extensive application of the crystals. Therefore, it is necessary to find a way to obtain reduced coenzyme Q10 powder and composition comprising the reduced coenzyme Q10 powder with smaller crystallinity, higher bioavailability and convenient application.

SUMMARY OF THE INVENTION

In order to overcome these deficiencies of the prior art, one of the purposes of the present invention is to provide a new reduced coenzyme Q10 powder, wherein there is a strong peak at the diffraction angle 2θ=18.9° and a strong absorption peak at 22.8° in Cu-Kα ray X-diffraction pattern, and also meet one or more of the following (a)-(d) items:

(a) the peak intensity at 22.8° is 100, the peak intensity at 20.0° is less than 40.0;

(b) the peak intensity at 22.8° is 100, the peak at 18.9° is less than 90.0;

(c) the intensity ratio of peak 27.4° to peak 18.9° is less than 0.1;

(d) the intensity ratio of peak 30.3° to peak 18.9° is less than 0.1.

Preferably, a melting point of the reduced coenzyme Q10 powder determined by DSC is 46.9° C. It is obviously lower than a melting temperature (49.5° C.) of crystals obtained by conventional solvent crystallization.

Another purpose of the present invention is to provide a method for preparing the reduced coenzyme Q10 powder, comprising the steps as follows: (1) adding or not adding an oxidized coenzyme Q10 to an organic solvent, heating to 50° C.~60° C. of temperature, and adding a reductant to the reaction, removing the organic solvent after finishing the reaction to obtain a molten and oily reduced coenzyme Q10 liquid; wherein the reductant is selected from one or more of hyposulphurous acid or salt thereof, ascorbic acid or salt thereof, carbodithioic acid or salt thereof and reductase; the organic solvent is hydrophilic alcohols, ketones, or hydrophobic alkanes; and (2) spraying the reduced coenzyme Q10 liquid in a sprayer, to form particles in cold air after spraying, to obtain a white reduced coenzyme Q10 powder.

Preferably, the hyposuphurous acid or salt thereof is thiosulfuric acid or sodium thiosulfate; the ascorbic acid or salt thereof is ascorbic acid or sodium ascorbate; the dithiosulfuric acid or salt thereof is dithiosulfuric acid or sodium dithiosulfate; the reductase is phosphorylation biological reductase; the hydrophilic alcohol is ethanol; the ketone is acetone; the hydrophobic paraffin is n-hexane.

Preferably, the temperature of the cold air is not higher than 30° C.; more Preferably, the temperature of the cold air is not higher than 10° C.

Preferably, the cold air is conventional air, air without oxygen or nitrogen.

Preferably, spraying by using centrifugal sprayer or pressure sprayer when spraying.

The method of the present invention further comprises adding antioxidant, stabilizer, absorption enhancer and/or excipient as adjuvants to the reduced coenzyme Q10 liquid before spraying, to obtain the reduced coenzyme Q10 powder with adjuvants; or re-melting the reduced coenzyme Q10 powder or the reduced coenzyme Q10 powder with the adjuvants, and then mixing it with antioxidant, stabilizer, absorption enhancer and/or excipient as adjuvants, to obtain the reduced coenzyme Q10 powder by a spraying drying method.

Preferably, the antioxidant is selected from one or more of vitamin E, butyl hydroxy toluene, ascorbic acid and vitamin A. The stabilizer is selected from one or more of gelatin, casein, sodium caseinate, soybean protein, modified starch, cyclodextrin and gum Arabic. The absorption enhancer is selected from one or more of polyglycerol fatty acid ester, glycerin, stearic acid, oleic acid and linoleic acid. The excipient is sugar and/or dextrin.

Preferably, antioxidants and/or stabilizers, and/or excipients, and/or absorption enhancer is added to the reduced coenzyme Q10 liquid, and then spraying in a sprayer, drying and styling the sprayed drops at 190° C. of temperature in hot air after spraying, to obtain the reduced coenzyme Q10 powder.

Preferably, the dosage form of the reduced coenzyme Q10 powder is tablets or capsules, for dietary supplement.

Another purpose of the present invention is to provide a composition comprising the reduced coenzyme Q10 powder, wherein the content of the reduced coenzyme Q10 powder of the composition is more than 10%.

Preferably, the dosage form of the reduced coenzyme Q10 powder is tablets or capsules, for dietary supplement.

In particular, the aforementioned method is to mix the oxidized coenzyme Q10 crystal with the reductant in molten or in organic solvents, and then remove the organic solvent by washing or volatilizing after finishing the reaction, to obtain the reduced coenzyme Q10 liquid in molten state, and then make the reduced coenzyme Q10 powdered by spraying in cool air, and finally obtain a dry power with lower crystals.

Moreover, in comparison with the crystals obtained by solvents or vegetable oil crystallization, the reduced coenzyme Q10 powder in Cu-Kα ray X diffraction pattern shows different characteristics of crystals and shows different melting points by Differential Scanning Thermal analyzer (DSC). More specifically, adding or not adding an organic solvent to oxidized coenzyme Q10, heating it to 60° C. of temperature, and then adding the reductant, and removing the organic solvent after finishing the reaction, to obtain an oily reduced coenzyme Q10 liquid.

The reductant in the reaction is selected from one or more of disulfurous acid or salts thereof, ascorbic acid or salt thereof, dithiosulfuric acid or salt thereof, enzymes, and so on.

The organic solvent in reaction may be hydrophilic organic solvents such as alcohols, ketones, and hydrophobic organic solvents such as alkane. It does also not add organic solvents due to the melting point of coenzyme Q10 nearly 50° C., it may directly heat the reacted liquid up to nearly 60° C., the reactants react with a reductant in the molten state.

If a hydrophilic organic solvent is used in the reaction, a plenty of water is added after finishing the reaction, the reaction temperature is kept at 60° C., placed to layer, remove water of the lower layer to make the organic solvent removed and wash out of unreacted reductant, to maintain the oil upper.

If a hydrophobic organic solvent is used in the reaction, a plenty of water is added for layering after finishing the reaction, to remove redundant reductant and water soluble impurities, to volatilize organic solvents of the organic layer in vacuum to obtain an oily reduced coenzyme Q10.

The oily reduced coenzyme Q10 is sprayed in a spraying drying tower. The difference from conventional blowing hot air in a spraying drying tower is that a cold air is blown into a spraying drying tower, due to the melting point of the reduced coenzyme Q10 nearly 50° C., the reduced coenzyme Q10 droplets immediately condenses into a white solid powder when blowing the cold air.

After melting the reduced coenzyme Q10 crystal, it may be used by centrifugal spraying or pressure spraying or other regular spraying. A spraying way of the present invention includes the temperature of the liquid before spraying is 55° C., the viscosity is 450 CPA, the rotational speed of atomizing disk is 15000 rpm, the particle diameter of the product is 180 μm. The parameters can be properly adjusted, according to different particle sizes of products and different methods of production.

During the process, the temperature of the cold air is not higher than 30° C., preferably is not higher than 10° C. The lower the temperature is, the more conducive to the cold cure of reduced coenzyme Q10 droplet. In order to prevent the oxidation of the reduced coenzyme Q10, preferably the blowing cold air is the air, the air without oxygen or nitrogen.

Moreover, in order to increase the stability or enhance the bioavailability of the reduced coenzyme Q10 dry powder, the coenzyme Q10 liquid in molten state can be added by suitable antioxidants such as vitamin E, butylated hydroxytoluene, ascorbic acid, vitamin A and so on, also can be added by absorption enhancers such as surfactant, glyceric acid, fatty acid, etc., according to needs.

Furthermore, in order to enhance the stability of the reduced coenzyme Q10 powder, the molten reduced coenzyme Q10 can be mixed with adjuvants before spraying, the adjuvants may be colloid such as gelatin, casein, sodium caseinate, soybean protein, starchy such as modified starch, cyclodextrin, polysaccharide such as gum Arabic; or a certain amount of excipients such as sugar, dextrin; or emulsifier, stabilizer, and then blow in hot air after mixing, and then to obtain the reduced coenzyme Q10 powder after spraying and drying.

By the method of the present invention, the reduced coenzyme Q10 obtained by the method of the present invention has a higher purity over 98%. The melting point thereof is lower than that of conventional solvent crystallization method, due to a stable crystallization has a higher melting point. A substable crystallization has a lower melting point. It is illustrated from these results that the crystallization degree of the reduced coenzyme Q10 declines, the amorphous degree thereof increases.

In comparison with the crystals crystallized by conventional solvent method, it may be shown from X diffraction pattern that the reduced coenzyme Q10 powder of the present invention obtained by spraying condensation has a very strong absorption peak at the diffraction angle 2θ=22.8° in the X-ray diffraction pattern, the intensity of a absorption peak is decreased obviously at other diffraction angle. Especially relative to the peak 18.9°, both of the intensity of peak 27.4° and peak 30.3° are less than 0.1; the intensity of peak 22.8° is 100, the intensity of peak 20.0° strength is less than 40.0, the intensity of peak 18.9° is less than 90.0.

For the crystals obtained by conventional solvent crystallization method, a strong absorption peaks appear at 3.0°, 4.6°, 20.1°, 22.8°, 27.4° and 30.3°. In particular, a strong absorption peak appears at 18.7° and 18.9°. And relative to peak 18.9°, the intensity of peak 27.4° and 30.3° is more than 0.1; the intensity of peak 22.8° is 100, the intensity of peak 20.0° strength is less than 40.0, the intensity of peak 18.9° is less than 200.0.

After the comparison, a strong peak at 18.7° in X-ray diffraction pattern of the reduced coenzyme Q10 powder of the present invention is disappeared, the intensity of other place peaks such as 3.0°, 4.6°, 18.9°, 20.1°, 22.8°, 27.4°, 30.3° 3.0° and 4.6°, 18.9° and 20.1° and 22.8° and 27.4° and 30.3° decreased significantly. The height of diffraction peak represents a size of the crystallinity. Therefore, the crystallinity of the reduced coenzyme Q10 powder of the present invention is decreased.

In addition, a white reduced coenzyme Q10 powder is used for a series of crystal characteristics analysis and biological utilization experiment in animals. The crystallinity reduction of pharmaceutical powder can increase the bioavailability of pharmaceuticals.

The reduced coenzyme Q10 powder with a reduced crystallinity obtained by the present invention, not only improves the stability, but also shows higher bioavailability in organisms. The reduced coenzyme Q10 powder can be used for foods, nutritions, health care products, cosmetics, pharmaceuticals and so on, and the application forms can be directly in the form of powder, tablet, capsule, or other appropriate composition by adding others such as excipients, colorants, antioxidants, diluent, absorption accelerants. The reduced coenzyme Q10 powder of the present invention is in incomplete crystallization and has good stability and excellent oral bioavailability, suitable for application in health food, cosmetics, medicines, etc.

DETAILED DESCRIPTION AND PREFERRED EMBODIMENTS THEREOF

Hereafter, the present invention will be described specifically with reference to the examples. The examples are given only for illustration of the technical solution of the present invention and should not be construed to limit the present invention.

Example 1

100 g oxidized coenzyme Q10 is added to 1000 mL n-hexane, heated to 50° C. of temperature after mixing. 1000 mL 20% (w/w) sodium thiosulfate solution is added to the reaction solution and stirred at 50° C. for 1 hour, and then layered to a water layer as a lower layer and a n-hexane layer after finishing the reaction, the n-hexane layer is washed by 25% (w/w) salt water, and then recycle n-hexane at 35° C. in vacuum, to form a paste and then heat the paste to 50° C. of temperature, spray by centrifugal sprayer, and form pellet at 10° C. in cold air after spraying, to obtain white reduced coenzyme Q10 powder 96.8 g (Sample 1) with the purity is 99.5% and the average powder particle size is 154 mm.

Experiment for Determining a Proportion of the Reduced Coenzyme Q10 in the Reduced Coenzyme Q10 Powder or Crystals by the HPLC Method Determining the proportion of reduced coenzyme Q10 in reduced coenzyme Q10 powder or crystals by the HPLC method. Determination conditions are as follows:
  Instruments: Agilent 1210
  Column: C18 column
  Mobile phase: ethanol/methanol=4/3(V/V)
  Detection wavelength: 210 nm
  Flow velocity: 1 ml/min The weight ratio of reduced coenzyme Q10 to oxidized coenzyme Q10 in Sample 1 by determination of the HPLC method is 99.2/0.8.

It can be seen from it that the reduced coenzyme Q10 has a higher purity than 98% in the reduced coenzyme Q10 powder of the present invention.

Experiment for Determining Diffraction Peaks of the Reduced Coenzyme Q10 Powder or Crystal by X-Ray Diffraction Determine the diffraction peak of the reduced coenzyme Q10 powder or crystal by X-ray diffraction method. It can determine from the X-ray diffraction pattern of diffraction peak position and intensity that the crystal shape changes. Determination of the present invention is made by a Cu-Kα ray X diffraction device. Determination conditions are as follows:
  Instrument models: X-ray powder diffraction Bruker D8 Advance
  Ray intensity: 40 kV、100 mA
  Angle range: 2θ=2~60°
  Scanning speed: 2°/min
  Scanning step: 0.05°
  Divergence slit: 1°
  Accept the slit: 0.60°
  Scattering slit: 1°

Figure 1:
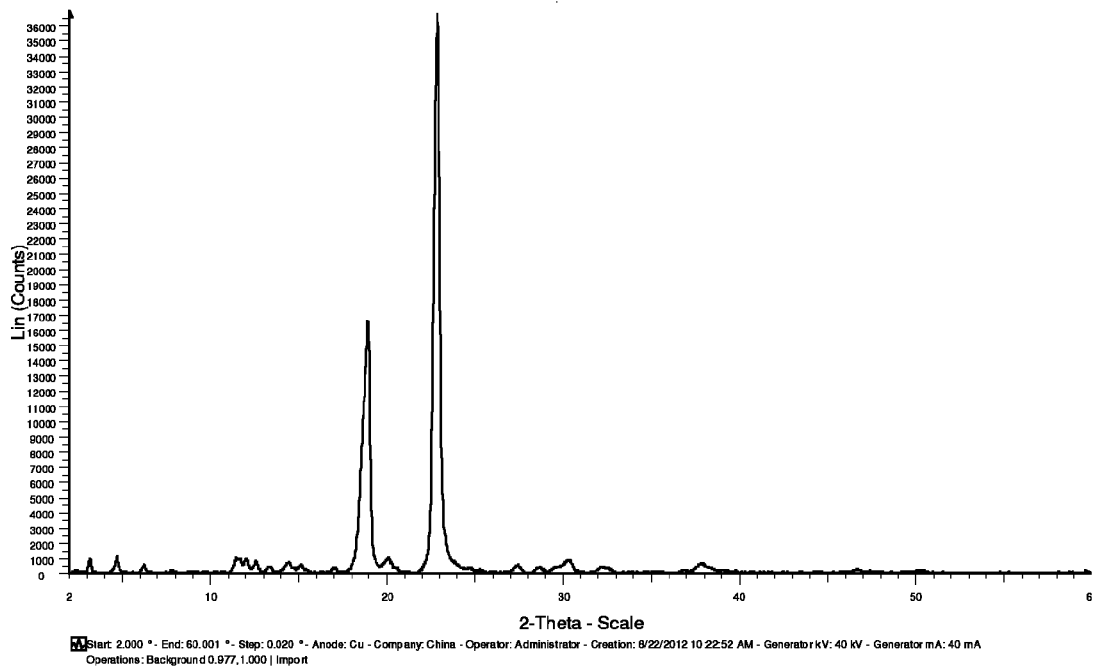
FIG. 1 is an X-ray diffraction pattern of the reduced coenzyme Q10 powder obtained by spraying oily reduced coenzyme Q10 in blowing cold air.

X-ray diffraction pattern of Samples 1 determined by the Cu-Kα ray X diffraction method is shown in FIG. 1. The diffraction angle 2θ in the diffraction pattern has a strong peak at 18.9°, and has a very strong absorption peak at 22.8°, and another diffraction angle peak intensity is decreased obviously, especially, a strength of peak 27.4° and 30.3° relative to peak 18.9° is less than 0.1. A peak strength at 22.8° is as 100. A peak strength at 20.0° is less than 40.0. A peak strength at 18.9° is less than 90.0.

Figure 3:
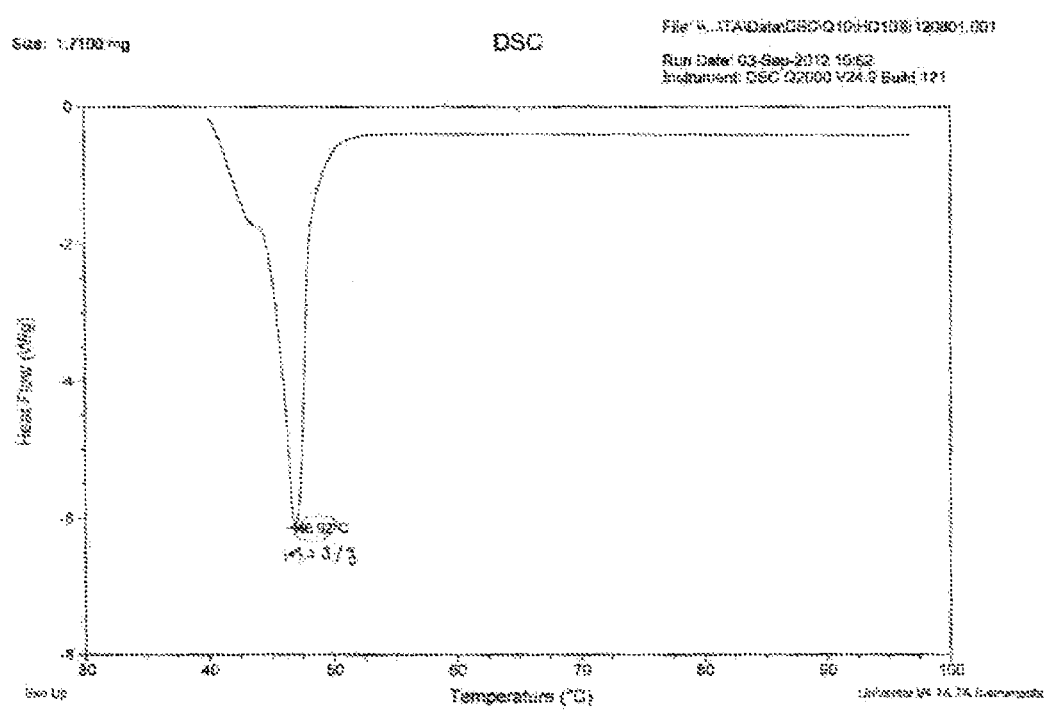
FIG. 3 is a DSC pattern of the reduced coenzyme Q10 powder obtained by spraying oily reduced coenzyme Q10 in blowing cold air.

Experiment for Determining the Melting Point of the Reduced Coenzyme Q10 Powder or Crystal by Thermogravimetric Analyzer Determine the melting point of the reduced coenzyme Q10 powder or crystal by thermogravimetric analyzer. Degree of amorphous and crystallization of reduced coenzyme Q10 can be determined by the melting point. Determination conditions of the present invention are as follows:
Instrument: Universal V4.7A TA Instruments
Temperature scope: 30-100° C.
Heating rate: 2.5° C./min
Sample amount: 15 mg Samples 1 is scanned for melting point by differential scanning thermal analyzer, its differential scanning map is shown in FIG. 3. It can be seen from it that the melting point is 46.9° C.

It can be seen from it that the crystal melting point of the present invention is lower than that of conventional solvent crystallization method, because the melting point of stable crystallization is higher, and the melting point of metastable crystallization is lower. The result illustrates that the crystallization degree of reduced coenzyme Q10 declines, its amorphous degree increases.

Example 2 (Comparative Example: Crystallization)

100 g oxidized coenzyme Q10 is added into 1000 mL n-hexane, heated to a 50° C. of temperature after mixing. 1000 mL 20% (w/w) sodium hydrosulfite solution is added to the reaction solution, and stirred at 50° C. for 1 hour and then. layered to a water layer as a lower layer and a n-hexane layer after finishing the reaction, the n-hexane layer is washed by 25% (w/w) salt water, and then recycle n-hexane at 35° C. in vacuum, to form a paste and then add 1100 ml of anhydrous ethanol and heated to 50° C. to be dissolved, then add 350 ml water to the solution under stirring, and cool to 5° C. to crystallization, to obtain 95.2 g white reduced coenzyme Q10 powder (sample Sample 2) after filtering and drying in vacuum, the purity is 99.4%, the average powder particle size is 148 mm.

According to the method of Example 1, the proportion of reduced coenzyme Q10 of Sample 2 is determined by HPLC method, the weight ratio of reduced coenzyme Q10 to oxidized coenzyme Q10 in Sample 2 is 99.0/1.0.

Figure 2:
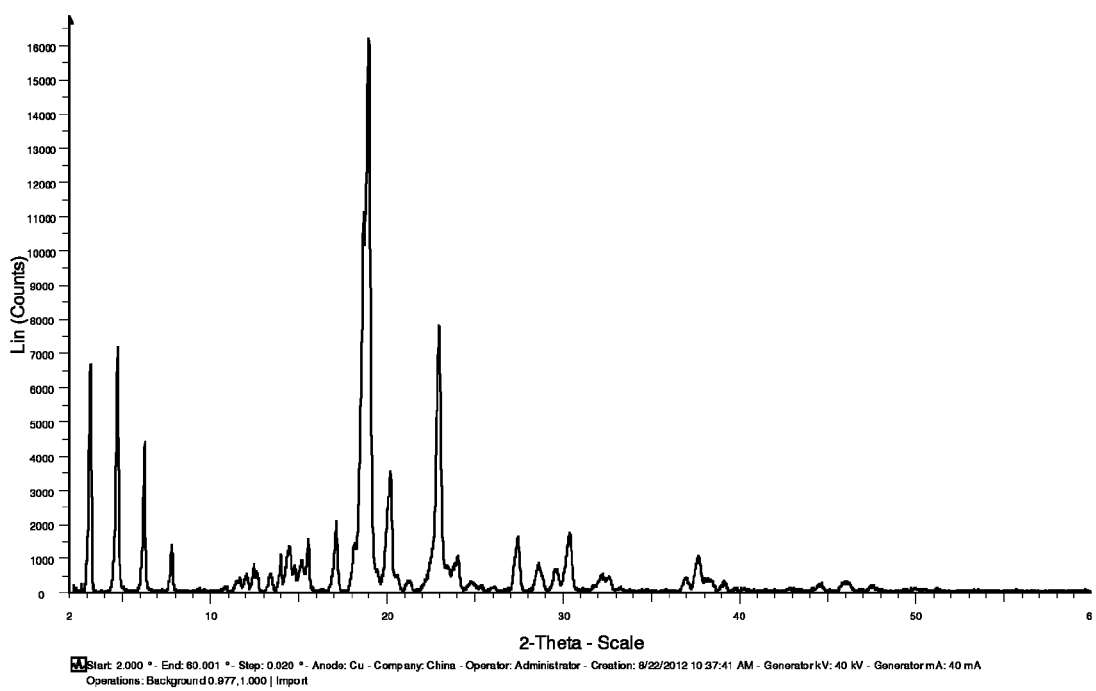
FIG. 2 is an X-ray diffraction pattern of the reduced coenzyme Q10 powder obtained by crystallization in ethanol solvent of conventional methods.

According to the method of Example 1, X-ray diffraction pattern of Samples 2 by the Cu-Kα ray X diffraction method is shown in FIG. 2. In the diffraction pattern, the diffraction Angle 2θ has strong peak at 3.0°, 4.6°, 20.1°, 22.8°, 27.4°, 30.3°, the diffraction Angle 2θ has a very strong absorption peak at 18.7°, 18.9°, and another diffraction Angle peak intensity is decreased obviously, the peak strength at peak 27.4° and 30.3° is less than 0.1 relative to peak 18.9°. A peak strength at 22.8° is as 100. A peak strength at 20.0° is less than 40.0. A peak strength at 18.9° is less than 90.0.

Figure 4:
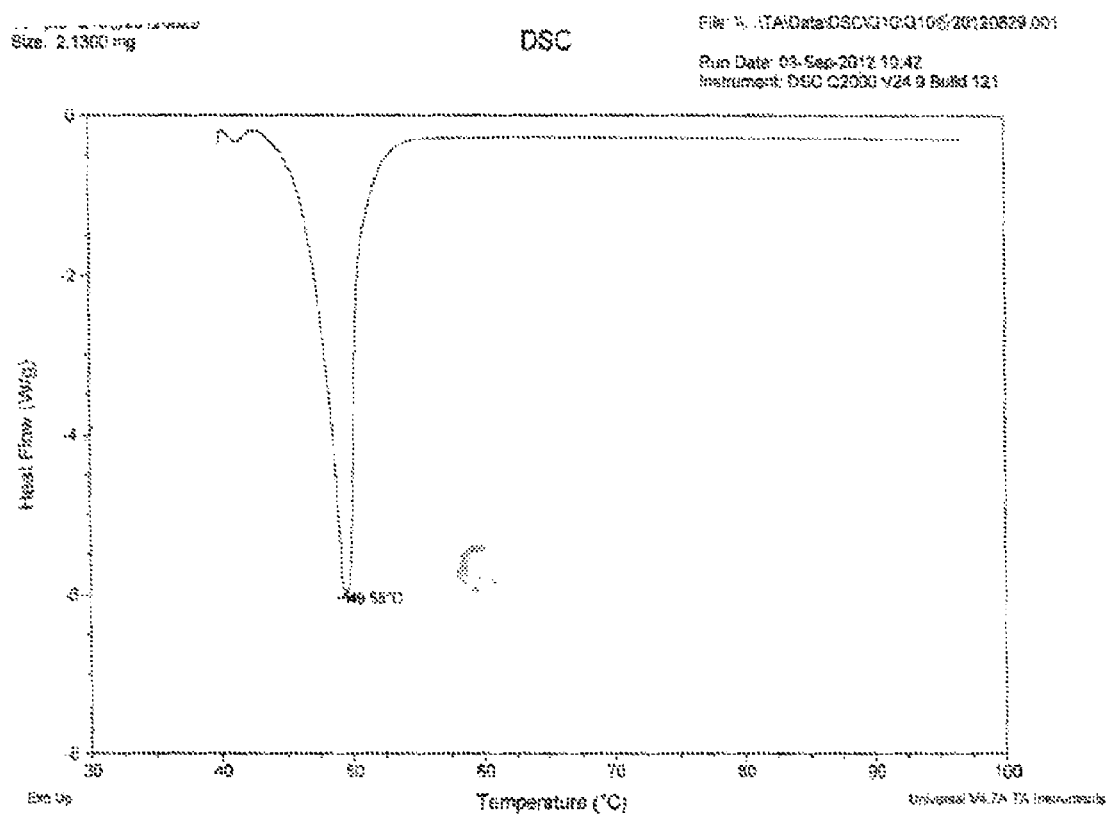
FIG. 4 is a DSC pattern of the reduced coenzyme Q10 powder obtained by crystallization in ethanol solvent of conventional methods.

According to the method of Example 1, the melting point of Sample 2 is determined by thermogravimetric analyzer, Samples 2 by differential scanning thermal analyzer is scanned for melting point. The differential scanning map is shown in FIG. 4, its melting point is 49.55° C.

Example 3 (Comparative Example: Crystallization)

30 g Sample 2 of Example 2 is dissolved in 20 times of sunflower oil, to dissolve under stirring at 60° C. of temperature, and then cool to 5° C. to crystallization, remove vegetable oil on the crystal surface with n-hexane after filtering, and dry under reduced pressure to obtain 25.6 g reduced coenzyme Q10 (Sample 3) with the purity of 98.9%.

According to the method of Example 1, the proportion of reduced coenzyme Q10 in Samples 3 is determined by HPLC method, the weight ratio of reduced coenzyme Q10 to oxidized coenzyme Q10 in Sample 2 is 99.1/0.9.

Example 4: Experiment Result of Stability

Sample 1 and Sample 2 and Sample 3 obtained by Example 1, Example 2, Example 3 are respectively stored under shading or nitrogen for two months at 18° C. The retention rate of reduced coenzyme Q10 is respectively determined within 1 month and 2 months. The results are in Table 1.

TABLE 1

| Sample | The retention rate of reduced coenzyme Q10 within 1 month | The retention rate of reduced coenzyme Q10 within 2 months |
| --- | --- | --- |
| Sample 1 | 98.4% | 95.5% |
| Sample 2 | 75.4% | 66.3% |
| Sample 3 | 89.3% | 85.4% |

It can be seen from the result of Table 1, the stability of the reduced coenzyme Q10 powder obtained by the method is the best one. It still reaches 95.5% after 2 months. It is higher than the reduced coenzyme Q10 obtained by conventional method, with levels of 66.3% of Samples 2, 85.4% of Sample 3.

Example 5: Experiment for Calculating Pharmacokinetic Parameters of Compounds and Relative Bioavailability Thereof Sample 1 and Sample 2 and Sample 3 obtained by Example 1, Example 2, Example 3 are used for beagle feeding experiment respectively, and the reduced coenzyme Q10 concentration in blood of feed beagle is determined, a basic pharmacokinetic parameters and relative bioavailability is calculated.

Experimental scheme is as follows:

4 beagles, half male and half female, 9-12 kg weight, provided by Shanghai Institute of Medicine Center for experimental animals, laboratory animals use license: SYXK (Shanghai), 2010-0049. A cross double cycle test is made. Gastric gavage is respectively for Sample 1, 2, 3, to fill stomach in a dose of 20 mg/kg, a delivery volume of 2 ml/kg. Samples with a suspension of soybean oil mixture for medicine (filling water 20 ml after feeding), normally feeding and drinking before testing, feeding feed containing meat on morning of the same day of feeding the medicine, to fill the stomach after 30 min. Two cycle tests are interval for a week.

Calculate the Pharmacokinetic Parameters of Compounds by WinNonlin 5.3 Software.

Peak-reaching time Tmax and peak-reaching concentration Cmax use measured values. Drug concentration area under time curve $AUC_{0-t}$ value is calculated by the trapezoidal method, $AUC_{0-\infty}$ is calculated by the formula $AUC_{0-\infty}=AUC_{0-t}+Ct/ke$. Ct is a concentration measured by the last time point, ke is an eliminate rate constant, with half logarithmic mapping method, calculation by eliminating the concentration of the phase; Plasma elimination half-life $t_{1/2}=0.693/ke$. Relative bioavailability F=($AUC_{0-t}$, Sample 2 or 3/AUC$_{0-t}$, Sample 1)×100%. The main pharmacokinetic parameters after Beagle lavage for 20 mg/kg sample. Refer to Table 2:

TABLE 2

| Sample | | T$_{max}$ (h) | C$_{max}$ (ng/ml) | AUC$_{0-t}$ (ng · h/ml) | AUC$_{0-\infty}$ (ng · h/ml) | MRT (h) | t$_{1/2}$ (h) | F (%) |
|---|---|---|---|---|---|---|---|---|
| Sample 1 | Average | 7.5 | 303 | 3640 | 2865 | 10.9 | 6.11 | / |
| | Standard deviation | 3.0 | 103 | 1833 | 2150 | 2.5 | 2.67 | / |
| Sample 2 | Average | 4.5 | 261 | 2359 | 2405 | 7.77 | 3.94 | 61.9 |
| | Standard deviation | 1.0 | 78 | 1181 | 1200 | 0.36 | 0.60 | 52.1 |
| Sample 3 | Average | 6.3 | 287 | 2765 | 2658 | 8.35 | 4.76 | 74.7 |
| | Standard deviation | 1.9 | 83 | 1237 | 1890 | 1.81 | 1.76 | 49.5 |

It can be seen from Table 2 that the bioavailability of reduced coenzyme Q10 powder (samples 1) obtained by the method in beagle is significantly higher than that of the other two ways.

It can be seen from Examples 1 to 5 that in comparison with the crystallization method of the present invention and the Comparative Examples, the reduced coenzyme Q10 liquid of the present invention is sprayed in a sprayer, and particles after spraying in cold air has a lower crystallinity, and higher stability and bioavailability.

Example 6

120 mL acetone and 80 mL deionized water are added to 60 g oxidized coenzyme Q10, heated under stirring to 50° C., stirring for 1.0 hr after adding 60 g ascorbic acid sodium. 150 mL n-hexane is added and placed after finishing the reaction, remove water of the lower layer, n-hexane of the upper layer is washed with 25% brine, and then to obtain a paste after recovering n-hexane, heat the paste up to 50° C. 1 g of natural vitamin E and 0.5 g ascorbic acid as an antioxidant is added to a sprayer, and spray through the pressure sprayer, fog droplets is at 0° C. nitrogen flow and shape immediately, finally obtain white reduced coenzyme Q10 powder 59.5 g. The purity is 96.3%, the average powder particle size is 210 mm.

According to the method of Example 1, the proportion of reduced coenzyme Q10 in the reduced coenzyme Q10 powder or crystals is determined by HPLC method, the proportion of reduced coenzyme Q10/oxidized coenzyme Q10 is 99.4/0.6.

The reduced coenzyme Q10 powder is mixed with safflower seed oil, beeswax, and lecithin, to form a soft capsule, wherein the content of the reduced coenzyme Q10 is 50 mg per soft capsule for a dietary supplement.

Example 7

1 g vitamin A as antioxidant is added to 30 g reduced coenzyme Q10 powder obtained by Example 6, and then mixed with 100 g gelatin, 100 g sugar, 35 g dextrin, 25 g glycerin solution to a pressure sprayer for spraying, droplets after spraying is in hot air of 190° C. to dry and shape immediately, to obtain 284.5 g a white reduced coenzyme Q10 powder. The content of reduced coenzyme Q10 is 10.6%.

According to the method of Example 1, the proportion of reduced coenzyme Q10 in the reduced coenzyme Q10 powder or crystals are determined by HPLC method, the proportion of reduced coenzyme Q10/oxidized coenzyme Q10 is 96.5/3.5.

Example 8

150 mL deionized water is added to 72 g oxidized coenzyme Q10, heated under stirring to 50° C., to add 35 g phosphorylation biological reductase for 4.0 hr and placed, to add 120 mL n-hexane to remove water of the lower layer, and wash out of n-hexane of the upper layer with 25% brine, to obtain paste after recovering n-hexane, the paste is heated up to 50° C., and then mixed with 0.5 g BHT, 0.5 g stearic acid, 3.0 g oleic acid, and 1.0 g linoleic acid in a pressure sprayer for spraying, droplets after spraying is in air without oxygen of 10° C. to dry and shape immediately, to obtain 60.5 g white reduced coenzyme Q10 powder, with a purity 45.9%, and an average powder particle size 192 mm.

Example 9

150 mL ethanol are added to 55 g oxidized coenzyme Q10, heated under stirring to 50° C., add 50 g carboxylic acid sodium disulfide under stirring for reaction 1.0 hr and placed after finishing the reaction, and add 120 mL n-hexane and 100 mL deionized water, remove water of the lower layer, and wash out of n-hexane of the upper layer with 25% brine, to obtain paste after recovering n-hexane, the paste is heated up to 50° C., and then mixed with 0.8 g antioxidant butylated hydroxy toluene (BHT) and 0.8 g vitamin A, 3.0 g polyglycerol fatty acid ester in a pressure sprayer for spraying, droplets after spraying is in nitrogen air of 30° C. to dry and shape immediately, to obtain white reduced coenzyme Q10 powder 53.5 g, with a purity of 90.9%, an average powder particle size of 203 mm.

Example 10

40 g reduced coenzyme Q10 powder of Example 9 is mixed with 25 g sodium caseinate, 18 g modified starch, 37 g cyclodextrin, 16 g gum Arabic, 10 g soybean protein solution in a centrifugal sprayer for spraying, droplets after spraying is in hot air of 180° C. to dry and shape immediately, to obtain white reduced coenzyme Q10 powder 142.5 g. The content of reduced coenzyme Q10 is 20.8%.

The present invention is illustrated by the above examples, however, should understand that the present invention is not limited to special instance and implementation scheme described here. These special examples and implementation plans is aimed at helping the person skilled in the art to practice the present invention. The persons skilled in the art is easily from the spirit and scope of the present invention to further improve and perfect, so the present invention only restricts by the content and scope of the claims of the present invention, and its intention to cover all in the alternative solutions and equivalent solutions which included in appendix claim limit within the scope of the invention spirit.

We claim:

1. A method for preparing a reduced coenzyme Q10 powder, wherein the method comprises:
   (1) adding an oxidized coenzyme Q10 into n-hexane to form a reaction solution, heating the reaction solution to 50° C.~60° C. temperature, adding a reductant for reacting with the heated reaction solution while, continuing to heat between 50° C.~60° C., after the reaction is complete, creating a layer of n-hexane, and washing the n-hexane layer with 25 w/w % salt water and recycling the n-hexane at 35° C. in vacuum to obtain a molten and oily reduced coenzyme Q10 liquid, wherein the reductant is selected from thiosulfuric acid or sodium thiosulfate; and
   (2) heating the molten and oily reduced coenzyme Q10 liquid to 50° C., and then spraying the molten and oily reduced coenzyme Q10 liquid in a centrifugal sprayer or pressure sprayer, to form particles in cold air of not higher than 30° C. after spraying, to obtain a white reduced coenzyme Q10 powder.

2. The method according to claim 1, wherein the cold air is cold air with oxygen, cold air without oxygen, or cold nitrogen.

3. The method according to claim 1, further comprising adding an antioxidant, stabilizer, absorption enhancer and/or excipient as adjuvants to the reduced coenzyme Q10 liquid before spraying, to obtain the reduced coenzyme Q10 powder with adjuvants; or re-melting the reduced coenzyme Q10 powder, and then mixing the re-melted reduced coenzyme Q10 powder with an antioxidant, stabilizer, absorption enhancer and/or excipient as adjuvants, to obtain the reduced coenzyme Q10 powder by a spraying drying method.

4. The method according to claim 3, wherein the antioxidant is selected from one or more of vitamin E, butyl hydroxy toluene, ascorbic acid and vitamin A; the stabilizer is selected from one or more of gelatin, casein, sodium caseinate, soybean protein, cyclodextrin and gum Arabic; the absorption enhancer is selected from one or more of polyglycerol fatty acid ester, glycerin, stearic acid, oleic acid and linoleic acid; and the excipient is sugar and/or dextrin.

5. The method according to claim 1, wherein a dosage form of the reduced coenzyme Q10 powder is tablets or capsules, for dietary supplement.

* * * * *